US011291621B2

(12) United States Patent
Maguyon et al.

(10) Patent No.: US 11,291,621 B2
(45) Date of Patent: Apr. 5, 2022

(54) TRANSPARENT SUNSCREEN COMPOSITION

(71) Applicant: Johnson & Johnson Consumer Inc., Skillman, NJ (US)

(72) Inventors: Elizabeth Maguyon, Lawrence Township, NJ (US); Frank C. Sun, Belle Mead, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/593,040

(22) Filed: Oct. 4, 2019

(65) Prior Publication Data
US 2021/0100734 A1   Apr. 8, 2021

(51) Int. Cl.
| A61K 8/891 | (2006.01) |
| A61K 8/35 | (2006.01) |
| A61K 8/37 | (2006.01) |
| A61Q 17/04 | (2006.01) |
| A61K 8/44 | (2006.01) |

(52) U.S. Cl.
CPC .............. *A61K 8/891* (2013.01); *A61K 8/35* (2013.01); *A61K 8/37* (2013.01); *A61K 8/44* (2013.01); *A61Q 17/04* (2013.01)

(58) Field of Classification Search
None
See application file for complete search history.

(56) References Cited

U.S. PATENT DOCUMENTS

| 5,306,486 | A * | 4/1994 | McCook | A61K 8/29 424/59 |
| 6,228,348 | B1 * | 5/2001 | Simon | A61K 8/91 424/59 |
| 8,236,287 | B2 | 8/2012 | Singleton | |
| 8,697,035 | B2 | 4/2014 | Singleton | |
| 9,144,535 | B1 | 9/2015 | Daly et al. | |
| 9,144,536 | B1 | 9/2015 | Daly et al. | |
| 2008/0014155 | A1 | 1/2008 | Marrs | |
| 2008/0025922 | A1 | 1/2008 | Marrs | |
| 2012/0015048 | A1 * | 1/2012 | Maitra | A61K 8/064 424/638 |
| 2012/0058192 | A1 * | 3/2012 | Singleton | A61K 8/062 424/493 |
| 2014/0044663 | A1 | 2/2014 | Do et al. | |
| 2014/0170192 | A1 * | 6/2014 | Halpern | A61K 8/8152 424/401 |
| 2017/0100323 | A1 * | 4/2017 | Matravers | A61K 47/28 |

FOREIGN PATENT DOCUMENTS

| DE | 202010006005 U1 | 7/2010 | |
| EP | 2509568 B | 10/2012 | |
| EP | 2550956 A1 * | 1/2013 | ............. A61K 8/891 |
| EP | 2604316 A | 6/2013 | |
| WO | WO 2008/117017 A | 10/2008 | |

OTHER PUBLICATIONS

Xiameter® reference 4 pages (Year: 2013).*
Silwax® D-02 Specification Sheet 1 page (Year: 2009).*
Silwax® D-02 MSDS 6 pages (Year: 2018).*
www.clearcoproducts.com/pdf/cosmetic/dimethicones/20cSt.pdf (Year: 2008).*
CVS Pharmacy SPF 30 Beach Guard Clear Spray (Year: 2017).*
Alcohol FDA Substance Registration (Year: 2017).*
Daylogic Sport Sunscreen SPF 50 (Year: 2018).*
Mintel Database, Defense Refresh Setting Mist SPF 50, Record 4775715, by Supergoop!, May 2017.
Mintel Database, Defense Refresh Setting Mist SPF 50, Record 5561449, by Supergoop! Corporate, Mar. 2018.
Mintel Database, Defense Refresh Setting Mist SPF 50, Record 6361789, by Supergoop! Corporate, Feb. 2019.
Mintel Database, Defense Refresh Setting Mist Sunscreen SPF 50 PA+++, Record 3184577, by Supergoop!, Jul. 2015.
Mintel Database, Defense Refresh Setting Mist Sunscreen SPF 50 PA+++, Record 3418039, by Supergoop!, Sep. 2015.
Mintel Database, Defense Refresh Setting Mist Sunscreen SPF 50 PA+++, Record 3953109, by Supergoop!, Apr. 2016.
Mintel Database, Green Tea & Aloe Makeup Setting Spray SPF 30, Record ID 4128607, by Coola, Jul. 2016.
Mintel Database, Green Tea & Aloe Makeup Setting Spray SPF 30, Record ID 4155247, by Coola, Jul. 2016.
ASTM International: "Standard Test Method for Viscosity of Silicone Fluids" D4283-98, Published Nov. 2015., pp. 1-2.
Database GNPD [Online] Mintel; Apr. 14, 2015 (Apr. 14, 2015). anonymous: 11 Waterproof UV Milk SPF50+/PA++++, XP055775982. Database accession No. 3126957 * the whole document *.
Database GNPD [Online] Mintel; Aug. 10, 2012 (Aug. 10, 2012). anonymous: 11 Wet Skin Sunblock Body Mist SPF 50 PA+++, XP055775986. Database accession No. 1849620 * the whole document *.
Database WPI Week 201776 Thomson Scientific. London. GB; AN 2017-70693Y XP002802109, & CN 107 233 220 A (Guangzhou Uniasia Cosmetics Technology) Oct. 10, 2017 (Oct. 10, 2017) * abstract *.
Search Report for EP20199930 dated Mar. 9, 2021.

* cited by examiner

*Primary Examiner* — Robert A Wax
*Assistant Examiner* — Caralynne E Helm

(57) ABSTRACT

The present invention provides a sunscreen composition comprising one or more oil soluble UV filters, at least about 20 weight percent ethanol, about 13.5 weight percent or less of a low viscosity silicone having a viscosity of at least 20 centistokes, and at least about 23 weight percent of a super low viscosity silicone having a viscosity up to about 15 centistokes, wherein the composition is anhydrous and transparent.

2 Claims, No Drawings

TRANSPARENT SUNSCREEN COMPOSITION

BACKGROUND OF THE INVENTION

It is well known that prolonged exposure to ultraviolet (UV) radiation, especially from the sun, can lead to the formation of light dermatoses and erythemas, and increase the risk of skin cancers, such as melanoma. Exposure to UV radiation also accelerates skin aging, such as loss of skin elasticity and wrinkling. For these reasons, sunscreen compositions are commonly used to provide photoprotection from the sun.

Sunscreen compositions often include one or more organic sunscreens to provide broad spectrum (UV-A and UV-B) protection. However, the high concentrations of organic sunscreens required to provide such protection often impart an oily feel to the compositions. One approach to reduce oiliness is to formulate sunscreens using an alcohol base. Alcohol-based sunscreen compositions can provide a pleasant and "clear" visual appearance. On the other hand, if not formulated correctly, alcohol-based sunscreens can have poor phase and viscosity stability, making them hazy in appearance and unacceptable to the consumer.

Silicones are also often employed in sunscreen compositions to provide pleasant, non-greasy aesthetics. For example, U.S. Pat. No. 8,236,287 relates to an oil-in-water sunscreen composition comprising at least 10 weight percent of an organic UV filter, a water-insoluble C2-C8 liquid silicone, a branched fatty acid ester of a polyprotic carboxylic acid, and at least 2 weight percent of a mineral particulate having a starch coating applied to the surface thereof. The liquid silicone may for example be ethyl methicone, and it is used in an amount of about 0.5 to about 10 percent of the composition.

It has now been discovered that a transparent, aesthetically pleasing, alcohol-based sunscreen composition may be made using UV filters, ethanol, and a high load of silicones. This was surprising because binary mixtures of silicone and ethanol, on the one hand, and silicones and UV filters, on the other, are typically immiscible. In addition, the silicones comprise a combination of low viscosity and super low viscosity silicones to provide reduced shine on the skin. The composition may additionally be substantially or completely free of oxybenzone while providing a surprisingly high SPF.

SUMMARY OF THE INVENTION

The present invention provides a sunscreen composition comprising one or more oil soluble UV filters, at least about 20 weight percent ethanol, about 13.5 weight percent or less of a low viscosity silicone having a viscosity of at least 20 centistokes, and at least about 23 weight percent of a super low viscosity silicone having a viscosity up to about 15 centistokes, wherein the composition is anhydrous and transparent.

DETAILED DESCRIPTION OF THE INVENTION

Unless defined otherwise, all technical and scientific terms used herein have the same meaning as commonly understood by one of ordinary skill in the art to which the invention belongs. All publications, patent applications, patents, and other references mentioned herein are incorporated by reference.

Where applicable, chemicals are specified according to their INCI Name. Additional information, including definitions, suppliers, and trade names, can be found under the appropriate INCI monograph in the *International Cosmetic Ingredient Dictionary and Handbook*, 16th Edition published by the Personal Care Products Council, Washington D.C. Also available via the Personal Care Products Council On-Line INFOBASE (online.personalcarecouncil.org/jsp/Home.jsp).
(http://online.personalcarecouncl.org/jsp/Home.jsp).

As used herein, "topically applying" means directly spraying, wiping, laying on, or spreading on outer skin or the scalp, e.g., by use of the hands or an applicator such as a wipe, roller, or spray.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "sunscreen composition" refers to a formulation (e.g. a lotion, spray, gel or other topical product) that absorbs and/or reflects some of the sun's ultraviolet (UV) radiation and thus helps protect against negative effects of sun exposure, e.g. sunburn, premature aging, etc.

As used herein, "cosmetically effective amount" means an amount of a physiologically active compound or composition sufficient for treating one or more conditions, but low enough to avoid serious side effects. The cosmetically effective amount of the compound or composition will vary with the condition being treated, the age and physical condition of the end user, the severity of the condition being treated/prevented, the duration of the treatment, the nature of other treatments, the specific compound or product/composition employed, the cosmetically-acceptable carrier utilized, and like factors.

As used herein, "cosmetically acceptable" means that the ingredients the term describes are suitable for use in contact with tissues (e.g., the skin) without undue toxicity, incompatibility, instability, irritation, allergic response, or the like.

As used herein, a "cosmetically acceptable active agent" is a compound (synthetic or natural) that has a cosmetic or therapeutic effect on the skin.

As used herein, "treatment or treating" refers to mitigating, reducing, preventing, improving, or eliminating the presence or signs of a condition or disorder.

"Phase stability" as used herein means the maintenance of interfacial stability or suspension stability or both at each of the temperatures 25° C., 40° C., and 50° C. for at least 2 weeks. "Interfacial stability" refers to stability against coalescence and coarsening of a discontinuous phase in a composition having two or more phases. "Suspension stability" refers to stability against creaming and/or sedimentation of a discontinuous phase, for example solids, suspended in continuous phase.

"Transparent" means free of undissolved particles and clear determined by visual inspection using a 20 mL glass scintillation vial.

As used herein, "substantially free of" means the ingredient referred to is not directly and intentionally added to the formula. Preferably, "substantially free of" means containing less than about 1% of an ingredient. More preferably "substantially free of" means containing less than about 0.5% of an ingredient. Even more preferably "substantially free of" means containing less than about 0.1% by weight of an ingredient. The composition may be completely free of an ingredient, i.e., contain none of the ingredient.

Unless otherwise indicated, a percentage or concentration refers to a percentage or concentration by weight (i.e., % (W/W)). Unless stated otherwise, all ranges are inclusive of the endpoints, e.g., "from 4 to 9" includes the endpoints 4 and 9.

UV Filter

The composition comprises one or more oil soluble UV filters.

As used herein, "organic UV filter" means an organic molecule capable of absorbing UV light, including: (i) aromatic compound conjugated with a carbonyl moiety substituted in the ortho- or para-position of the aromatic ring, and (ii) polymers made of organic chromophores attached to a polymer chain, either of which block or absorb ultraviolet (UV) light.

Traditional organic UV filters are aromatic, small molecules with molecular weight values <900 g/mol. Examples of organic non-polymeric UV filters include, but are not limited to: methoxycinnamate derivatives such as octyl methoxycinnamate and isoamyl methoxycinnamate; camphor derivatives such as 4-methyl benzylidene camphor, camphor benzalkonium methosulfate, and terephthalylidene dicamphor sulfonic acid; salicylate derivatives such as octyl salicylate, ethylhexyl salicylate and homosalate; benzone derivatives such as dioxybenzone, and oxybenzone; benzoic acid derivatives such as aminobenzoic acid and octyldimethyl para-amino benzoic acid; octocrylene and other β,β-diphenylacrylates; dioctyl butamido triazone; octyl triazone; avobenzone (butyl methoxydibenzoylmethane); menthyl anthranilate; triazone derivatives such as ethylhexyl triazone (Uvinul® T150); diethylhexyl butamido triazone (UVA-Sorb® HEB); bis-ethylhexyloxyphenol methoxyphenyl triazine (Tinosorb® S), benzoate derivatives such as diethylamino hydroxybenzoyl hexyl benzoate (Uvinul® A Plus), benzotriazole derivatives such as drometrizole trisiloxane (Mexoryl® XL), methylene bis-benzotriazolyl tetramethylbutylphenol (Tinosorb® M); tris-biphenyl triazine; (2-{4-[2-(4-Diethylamino-2-hydroxy-benzoyl)-benzoyl]-piperazine-1-carbonyl}-phenyl)-(4-diethylamino-2-hydroxy-phenyl)-methanone; merocyanine derivatives; bis (butylbenzoate) diaminotriazine aminopropylsiloxane; and bis-ethylhexyloxyphenol methoxyphenyl triazine, encapsulated in a polymer matrix.

Polymeric, organic UV filters are polymers made of organic chromophores attached to polymer chains, for instance a polysiloxane chain having for example an average molecular weight of >6000 Daltons. Examples of such polysiloxane UV filters include, without limitation Parsol® SLX and polysilicone-15. These polysiloxanes absorb in the UVB ($\lambda_{max}$=312 nm) part of the spectrum and are typically combined with UVA filters to achieve broad-spectrum protection.

The following table lists various commercially available organic UV filters.

| UV Filter | Other names | Coverage |
| --- | --- | --- |
| Benzophenone-3 | Oxybenzone or 2-hydroxy-4-methoxybenzophenone | UVA/B |
| Benzophenone-5 | 2-hydroxy-4-methoxybenzophenone-5-sulfonic acid (benzophenone-5) and its sodium salt<br>Sulizobenzone sodium<br>Sodium hydroxymethoxybenzophenone sulfonate | UVA/B |
| Benzophenone-8 | Dioxybenzone or 2,2'-dihydroxy-4-methoxybenzophenone dioxybenzone (2-hydroxy-4-methoxyphenyl)(2-hydroxyphenyl)methanone methanone, (2-hydroxy-4-methoxyphenyl)(2-hydroxyphenyl) | UVA/B |
| 3-benzylidene camphor | 3-benzylidene camphor | UVB |
| Bis ethylhexyloxyphenol methoxyphenyl triazine | Tinosorb S or (1,3,5)-triazine-2,4-bis{[4-(2-ethyl-hexyloxy)-2-hydroxy]-phenyl)-6-(4-methoxyphenyl) or anisotriazine | UVA/B |
| Butylmethoxy dibenzoyl methane | Avobenzone or 1-(4-tert-butylphenyl)-3-(4-methoxyphenyl) propane-1,3-dione | UVA |
| Camphor benzalkonium Methosulfate | Mexoryl SO or N,N,N-trimethyl-4-(2-oxoborn-3-ylidene-methyl) anilinium methyl sulphate | UVB |
| Diethylamino hydroxybenzoyl hexyl benzoate | Uvinul A plus or benzoic acid, 2-[-4-(diethylamino)-2-hydroxybenzoyl]-, hexylester | UVA |
| Diethylhexyl butamido triazone | UVASorb HEB or benzoic acid, 4,4-((6-((4-(((1,1-dimethylethyl) amino) carbonyl) phenyl) amino) 1,3,5-triazine-2,4-diyl) diimino) bis-(2-) ester) or dioctyl butamido triazone | UVB |
| Drometrizole trisiloxane | Mexoryl XL or phenol,2-(2H-benzotriazol-2-yl)-4-methyl-6-(2-methyl-3-(1,3,3,3-tetramethyl-1-(trimethylsilyl)oxy)-disiloxanyl)propyl) | UVA/B |

-continued

| UV Filter | Other names | Coverage |
| --- | --- | --- |
| Ethoxyethyl methoxycinnamate | Cinoxate | UVB |
| Ethylhexyl dimethylamino Benzoate | Padimate O<br>Octyl dimethyl PABA<br>Ethylhexyl dimethyl PABA | UVB |
| Ethylhexyl methoxycinnamate | OMC or octinoxate<br>Octyl methoxycinnamate | UVB |
| Ethylhexyl salicylate | Octisalate<br>2-ethylhexyl salicylate<br>Octyl salicylate | UVB |
| Ethylhexyl triazone | Uvinul T150<br>2,4,6-trianilino-(p-carbo-2'-ethylhexyl-1'oxy)-1,3,5-triazine<br>Octyl triazone | UVB |
| Homosalate | 3,3,5-trimethylcyclohexyl 2-hydroxybenzoate<br>Salicilato de homomentila | UVB |
| Isoamyl p-methoxycinnamate | Amiloxate<br>Isopentyl-4-methoxycinnamate | UVB |
| Methyl anthranilate | Meradimate | UVA |
| 4-methylbenzylidene camphor | Enzacamene<br>3-(4'-methylbenxylidene)d-1 camphor<br>4 MBC | UVB |
| Methylene bis-benzotriazolyl tetramethylbutylphenol | Tinosorb M<br>2,2'-methylene-bis-6-(2H-benzotriazol-2yl)-4-(tetramethyl-butyl)-1,1,3,3-phenol | UVA/B |
| Octocrylene | 2-cyano-3,3-diphenyl acrylic acid, 2-ethylhexyl ester | UVB |
| Para aminobenzoic acid | PABA<br>4-aminobenzoic acid | UVB |
| Polyacrylamido methylbenzylidene Camphor | Mexoryl SW<br>Polymer of N-[(2 and 4)-[(2-oxoborn-3-ylidene)methyl]benzyl]acrylamide | UVB |
| Polysilicone-15 | Parsol SLX<br>Diethylbenzylidene malonate Dimethicone<br>Diethylmalonylbenzylidene Oxypropene dimethicone<br>Dimethicodiethylbenzalmalonate | UVB |
| Triethanolamine salicylate | Neo Heliopan TES<br>Trolamine salicylate | UVB |
| Terephtalydene dicamphor sulfonic acid | Mexoryl SX | UVA |

The sunscreen composition may comprise at least about 10 weight percent of one or more oil soluble UV filters based on the total weight of the composition. The composition may comprise about 15 to about 35 weight percent of one or more oil soluble UV filters based on the total weight of the composition. The composition may comprise at least about 21 weight percent of one or more oil soluble filters based on the total weight of the composition, particularly when a transparent composition is desired.

The oil soluble UV filters may be selected from one or more of homosalate, octisalate, avobenzone, octocrylene.

The oil soluble UV filters may be a mixture of homosalate, octisalate, avobenzone, octocrylene. For example, the sunscreen composition may comprise about 8 to about 15 weight percent homosalate, about 4 to about 5 weight percent octisalate, about 2 to about 3 weight percent avobenzone, and about 7 to about 10 weight percent octocrylene, based on the total weight of the composition.

The sunscreen composition may be substantially free of oxybenzone. The sunscreen composition may be completely free of oxybenzone.

The composition may optionally contain one or more UV blockers, which are compounds that reflect, absorb or scatter the UV radiation. When present in sunscreen compositions they reflect the ultraviolet, visible and infrared rays to enhance sun protection. UV blockers are typically inorganic metallic oxides, including titanium dioxide, zinc oxide, and certain other transition metal oxides. Such UV blockers are typically solid particles in a micronized or nanonized form having a diameter from about 0.01 micron to about 10 microns.

Examples include zinc oxide, titanium dioxide, doped zinc oxide, doped titanium dioxide, and other transition metal oxides. Doped metal oxides contain dopants that are trace elements of other metal atoms incorporated into the crystal lattice of the primary metal oxide to modify its electrical or optical properties and may include aluminum, manganese, and iron.

In another embodiment, the metal oxide comprises coated particles. The coating may comprise for example hydrophobic materials such as alkyl siloxanes (e.g. triethoxycaprylylsilane), silicones or metal salts of fatty acids.

In one embodiment, the metal oxide comprises particles having a diameter from about 0.01 micron to about 10 microns.

In one embodiment, the inorganic sunscreen may further comprise particulate doped zinc oxides as referred in U.S. Pat. Nos. 9,144,535, 9,144,536 and WO2008117017, incorporated herein by reference in their entirety. Such particulate zinc oxides comprise low levels of certain dopants at particular ratios and provide improved performance with respect to absorption in the UVA portion of the electromagnetic spectrum. The particulate zinc oxides comprise a cationic portion that in turn comprises about 99% by weight or more of a zinc portion. The cationic portion further comprises first and second dopant portions comprising metals such as manganese, iron, aluminum, and copper. The first and second dopant portions may be present in amounts of about 0.1% to about 0.75% by weight of the cationic portion. The particulate doped zinc oxides may further comprise additional metal cations, for example, cations of alkali metals, alkaline earth metals, other transition metals, as well as cations of metals such as gallium, germanium, gallium, indium, tin, antimony, thallium, lead, bismuth, and polonium, in small concentrations.

These doped zinc oxides may be made by various methods, such as by reducing oxide ores using, for example, carbon or other suitable reducing agents, and then re-oxidizing. Other suitable methods include wet chemical methods. One example of a wet chemical method includes mixing alkaline salt solutions of the various cations and causing ZnO to precipitate by reducing the pH using an acid such as oxalic or formic acid. A particularly suitable wet chemical method is the so-called "sol-gel" method.

SPF

Sun protection factor (SPF) may be tested using the following IN VITRO SPF TEST METHOD. The baseline transmission of a PMMA plate (substrate, available from Helioscience, Marseille, France) is measured for UV absorbance using calibrated Labsphere® UV-10005 UV transmission analyzer or a Labsphere® UV-20005 UV transmission analyzer (Labsphere, North Sutton, N.H., USA). A test sample is then applied to the PMMA plate using an application density of about 1.3 mg/cm$^2$ by rubbing into a uniform thin layer with the operator's finger. The sample is allowed to dry for 15 minutes and then measured for UV absorbance in the same way. The absorbance measures are used to calculate SPF as known in the art using the following equation:

$$SPF \text{ in vitro} = \frac{\int_{\lambda=290\,nm}^{\lambda=400\,nm} E(\lambda) * I(\lambda) * d\lambda}{\int_{\lambda=290\,nm}^{\lambda=400\,nm} E(\lambda) * I(\lambda) * 10^{A_0(\lambda)} * d\lambda}$$

in which:
$E(\lambda)$=Erytheme action spectrum;
$I(\lambda)$=Spectral irradiance received from the UV source;
$A_0(\lambda)$=Mean monochromatic absorbance of the test product layer before UV exposure; and
$d(\lambda)$=Wavelength step (1 nm).

In one embodiment, the composition has an SPF as measured by the IN VITRO SPF TEST METHOD of at least about 15. In another embodiment, the composition has an SPF as measured by the IN VITRO SPF TEST METHOD of at least about 25.

The composition may comprise one or more SPF boosters, such as styrene/acrylates copolymer. A commercially available styrene/acrylates copolymer is SUNSPHERES Powder from Dow Chemical.

Film Formers

Film formers are generally polymers that, when dissolved in a composition, permit a continuous or semi-continuous film to be formed when the composition is spread onto, e.g., smooth glass, and the liquid vehicle is allowed to evaporate. As such, the polymer should dry on the glass in predominantly continuous manner, rather than forming a plurality of discrete, island-like structures. Generally, the films formed by applying the sunscreen compositions on the skin according to the invention are less than, on average, about 100 microns in thickness, such as less than about 50 microns.

Suitable film-forming polymers include natural polymers such as polysaccharides or proteins and synthetic polymers such as polyesters, polyacrylics, polyurethanes, vinyl polymers, polysulfonates, polyureas, polyoxazolines, and the like. Specific examples of film-forming polymers include, for example, acrylic homopolymers or copolymers with hydrophobic groups such as Acrylates/Octylacrylamide Copolymer including DERMACRYL 79 available from Akzo Chemical of Bridgewater, N.J.; Acrylates/Dimethicone Acrylate Copolymer available as X-22-8247D from Shin-Etsu of Japan; Hydrogenated Dimer Dilinoleyl/Dimethylcarbonate Copolymer, available from BASF Corp. as COSMEDIA DC; copolymer of vinylpyrrolidone and a long-chain alpha-olefin, such as those commercially available from Ashland Specialty Ingredients as GANEX V220; vinylpyrrolidone/tricontanyl copolymers available as GANEX WP660 also from Ashland; water-dispersible polyesters, including sulfopolyesters such those commercially available from Eastman Chemical as EASTMAN AQ 38S. In certain embodiments, the film-forming polymer is water insoluble, but is rendered soluble upon exposure to alkalinity in order to facilitate removal from the skin upon washing with soap.

The total amount of film formers in the composition may range from about 0.25% to about 15% by weight of the composition based on the total weight of the composition. The total amount of film formers in the composition may range from about 0.5% to about 10% by weight of the composition based on the total weight of the composition. The total amount of film formers in the composition may range from about 1% to about 5% by weight of the composition based on the total weight of the composition by weight of the composition based on the total weight of the composition.

Low Viscosity Silicone

The composition contains one or more low viscosity silicones. Silicones, also known as polysiloxanes, are polymers made of repeating units of siloxane, a chain of alternating silicon atoms and oxygen atoms, combined with carbon, hydrogen, and sometimes other elements.

The low viscosity silicone should have the lowest viscosity that will not evaporate in an open system. The low viscosity silicone may have a viscosity of at least 20 centistokes. The low viscosity silicone may have a viscosity of at least 50 centistokes. The low viscosity silicone may have a viscosity of at least 100 centistokes.

"Viscosity" as used herein means kinematic viscosity, which is a measure of volume flow of a liquid, defined as a stoke (St). A centistoke, cSt=0.01 St=1 mm$^2$/sec. "ASTM Designation: D4283-98- Standard Test Method for Viscosity of Silicone Fluids" may be used to determine the viscosity. In this test method it is recommended to use an Ostwald Viscometer (up to 5,000 cst), Ubbelohde Viscometer (up to 100,000 cst) or a Cannon Fenski Viscometer (up to 5,000 cst) when determining the kinematic viscosity.

The low viscosity silicone may be dimethicone having a viscosity of at least 20 centistokes. The low viscosity silicone may be dimethicone having a viscosity of at least 50 centistokes. The low viscosity silicone may be dimethicone having a viscosity of at least 100 centistokes.

Dimethicones having viscosities of 20 or 50 or 100 centistokes are commercially available for example from Dow Chemical Company (Midland, Mich.).

The amount of low viscosity silicone in the composition may range up to about 13.5 percent by weight of the total weight of the composition. The amount of low viscosity silicone in the composition may range from about 1 to about 13.5 percent by weight based on the total weight of the composition.

Super Low Viscosity Silicone

The super low viscosity silicone is characterized by its fast evaporation rate. Also a silicone or polysiloxane, it has a viscosity up to about 15 centistokes. The super low viscosity silicone may have a viscosity up to about 6 centistokes. The super low viscosity silicone may have a viscosity up to about 2 centistokes. Viscosity is kinematic viscosity and may be measured as set forth above.

The super low viscosity silicone may be linear rather than cyclic.

The super low viscosity silicone may be 2 centistoke dimethicone (and) trisiloxane. Two centistoke dimethicone (and) trisiloxane is commercially available from Dow Chemical Company (Midland, Mich.).

The super low viscosity silicone may be ethyl methicone having a viscosity of 6 to 15 centistokes. Such ethyl methicone is commercially available from Siltech Corp (Toronto, Canada).

The amount of super low viscosity silicone in the composition may be at least about 23 weight percent of the total weight of the composition. The amount of super low viscosity silicone in the composition may range from about 23 to about 58 percent by weight based on the total weight of the composition.

Ethanol

The sunscreen composition is anhydrous. The composition may be substantially free of water. The composition may be completely free of water.

The sunscreen composition comprises ethanol.

The composition may comprise at least about 20 weight percent ethanol. The composition may comprise at least about 25 weight percent ethanol. The composition may comprise at least about 30 weight percent ethanol.

Topical Composition

The composition may be prepared using mixing and blending methodology well known in the sunscreen and cosmetic art.

The composition may be combined with a "cosmetically-acceptable topical carrier," i.e., a carrier for topical use that capable of containing the other ingredients dispersed or dissolved therein, and possessing acceptable properties rendering it safe to use topically.

The cosmetically-acceptable topical carrier may optionally comprise a wide variety of additional oil-soluble materials and/or oil-dispersible materials conventionally used in compositions for use on skin, at their art-established levels. For example, surfactants, emulsifiers, pearlescent or opacifying agents, thickeners, emollients, conditioners, humectants, chelating agents, exfoliants, preservatives, pH adjusting agents, and additives that enhance the appearance, feel, or scent of the composition, such as colorants, fragrances, tactile modifiers, and the like, can be included.

The composition may optionally comprise additional film formers for instance natural polymers such as polysaccharides or proteins and synthetic polymers such as other polyesters, polyacrylics, polyurethanes, vinyl polymers, polysulfonates, polyureas, polyoxazolines, and the like. Specific examples include acrylates/dimethicone acrylate copolymer (commercially available as X-22-8247D from Shin-Etsu of Japan); hydrogenated dimer dilinoleyl/dimethylcarbonate copolymer (commercially available from BASF Corp. as COSMEDIA DC); copolymers of vinylpyrrolidone and a long-chain alpha-olefin (such as those commercially available from Ashland Specialty Ingredients as GANEX V220); vinylpyrrolidone/tricontanyl copolymers (commercially available as GANEX WP660 also from Ashland).

Suitable emollients include mineral oils, petrolatum, vegetable oils (e.g. triglycerides such as caprylic/capric triglyceride), waxes and other mixtures of fatty esters, including but not limited to esters (e.g, isopropyl palmitate, isopropyl myristate, diisopropyl adipate, dibutyl adipate, dicaprylyl carbonate, C12-15 alkyl benzoate), silicone oils such as dimethicone, and alkanes such as isohexadecane.

In certain embodiments, the composition includes a pigment suitable for providing color or hiding power. The pigment may be one suitable for use in a color cosmetic product, including compositions for application to the hair, nails and/or skin, especially the face. Color cosmetic compositions include, but are not limited to, foundations, concealers, primers, blush, mascara, eyeshadow, eyeliner, lipstick, nail polish and tinted moisturizers. The pigment suitable for providing color or hiding power may be composed of iron oxides, including red and yellow iron oxides, titanium dioxide, ultramarine and chromium or chromium hydroxide colors, and mixtures thereof. The pigment may be a lake pigment, e.g. an organic dye such as azo, indigoid, triphenylmethane, anthraquinone, and xanthine dyes that are designated as D&C and FD&C blues, browns, greens, oranges, reds, yellows, etc., precipitated onto inert binders such as insoluble salts. Examples of lake pigments include Red #6, Red #7, Yellow #5, Violet #2 and Blue #1. The pigment may be an interference pigment. Examples of interference pigments include those containing mica substrates, bismuth oxychloride substrates, and silica substrates, for instance mica/bismuth oxychloride/iron oxide pigments commercially available as CHROMALITE pigments (BASF), titanium dioxide and/or iron oxides coated onto mica such as commercially available FLAMENCO pigments (BASF), mica/titanium dioxide/iron oxide pigments including commercially available KTZ pigments (Kobo products), CELLINI pearl pigments (BASF), and borosilicate-containing pigments such as REFLECKS pigments (BASF).

In one embodiment, the composition comprises a humectant such as butylene glycol or glycerin. The composition may comprise for example at least about 1.0 weight percent of a humectant.

The composition may further comprise one or more other cosmetically acceptable active agents include for example anti-acne agents, shine control agents, anti-microbial agents, anti-inflammatory agents, anti-mycotic agents, anti-parasite agents, external analgesics, antioxidants, keratolytic agents, moisturizers, nutrients, vitamins, energy enhancers, anti-perspiration agents, astringents, deodorants, firming agents, anti-callous agents, and agents for skin conditioning.

The amount of other cosmetically active agents may range from about 0.001% to about 20% by weight of the composition, e.g., about 0.005% to about 10% by weight of the composition, such as about 0.01% to about 5% by weight of the composition.

The cosmetically acceptable active agent may be selected for instance from D-panthenol carotenoids, ceramides, polyunsaturated fatty acids, essential fatty acids, enzymes such as laccase, enzyme inhibitors, minerals, steroids such as hydrocortisone, 2-dimethylaminoethanol, copper salts such as copper chloride, peptides like argireline, syn-ake and those containing copper, coenzyme Q10, amino acids such as proline, vitamins, lactobionic acid, acetyl-coenzyme A, niacin, riboflavin, thiamin, ribose, electron transporters such as NADH and FADH2, natural extracts such as from aloe vera, feverfew, oatmeal, dill, blackberry, princess tree, *Picia anomala*, and chicory, resorcinols such as 4-hexyl resorcinol, curcuminoids, sugar amines such as N-acetyl glucosamines, and derivatives and mixtures thereof.

Examples of vitamins include, but are not limited to, vitamin A, vitamin B's such as vitamin B3, vitamin B5, and vitamin B12, vitamin C, vitamin K, and different forms of vitamin E like alpha, beta, gamma or delta tocopherols or their mixtures, and derivatives thereof.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

Sprayability

The composition of the invention is sprayable. "Sprayable" as used herein means the composition, when manually actuated or through pressurized release out of a dispensing mechanism, such as a bottle with pump spray nozzle or an aerosol can, creates a spray pattern evenly distributed and reproducible over an area of a defined shape (e.g. circle, annulus) and size. The composition may be sprayable without the use of propellants, i.e., in non-aerosol form.

The following non-limiting examples further illustrate the invention.

EXAMPLE 1

A series of compositions were made using 30 wt % Ethanol, Dimethicone (20 cst), Dimethicone (and) Trisiloxane and the other ingredients shown in Table 1. Compositions 1-6 were according to the invention and Compositions A and B were comparative.

TABLE 1

| INCI | Weight (%) | | | | | | | |
|---|---|---|---|---|---|---|---|---|
|  | Comp. 1 | Comp. 2 | Comp. 3 | Comp. 4 | Comp. 5 | Comp. 6 | Comp. A | Comp. B |
| Avobenzone | 3 | 3 | 3 | 3 | 3 | 3 | 3 | 3 |
| Octisalate | 5 | 5 | 5 | 5 | 5 | 5 | 5 | 5 |
| Homosalate | 10 | 10 | 10 | 10 | 10 | 10 | 10 | 10 |
| Octocrylene | 10 | 10 | 10 | 10 | 10 | 10 | 10 | 10 |
| Acrylates/Octylacryl amide Copolymer | 1 | 1 | 1 | 1 | 1 | 1 | 1 | 1 |
| Dimethicone; Acrylates/Dimethicone Copolymer | 1 | 1 | 1 | 1 | 1 | 1 | 1 | 1 |
| Ethanol | 30 | 30 | 30 | 30 | 30 | 30 | 30 | 30 |
| Dimethicone (and) Trisiloxane | 31.8 | 34.3 | 29.3 | 26.8 | 24.3 | 23.3 | 22.8 | 21.8 |
| Diisopropyl Adipate | 3 | 3 | 3 | 3 | 3 | 3 | 3 | 3 |
| Tocopheryl Acetate | 0.2 | 0.2 | 0.2 | 0.2 | 0.2 | 0.2 | 0.2 | 0.2 |
| Dimethicone (20 cst) | 5 | 2.5 | 7.5 | 10 | 12.5 | 13.5 | 14 | 15 |

Another series of compositions were made using 30 wt % Ethanol, Dimethicone (20 cst), Ethyl Methicone and the other ingredients shown in Table 2. Compositions 7-9 were according to the invention, and Compositions C-G were comparative.

TABLE 2

| INCI | Weight (%) | | | | | | | |
|---|---|---|---|---|---|---|---|---|
|  | Comp. 7 | Comp. 8 | Comp. 9 | Comp. C | Comp. D | Comp. E | Comp. F | Comp. G |
| Avobenzone | 3 | 3 | 3 | 3 | 3 | 3 | 3 | 3 |
| Octisa late | 5 | 5 | 5 | 5 | 5 | 5 | 5 | 5 |
| Homosalate | 10 | 10 | 10 | 10 | 10 | 10 | 10 | 10 |
| Octocrylene | 10 | 10 | 10 | 10 | 10 | 10 | 10 | 10 |
| Acrylates/Octyla crylamide Copolymer | 1 | 1 | 1 | 1 | 1 | 1 | 1 | 1 |
| Dimethicone; Acrylates/Dimet hicone Copolymer | 1 | 1 | 1 | 1 | 1 | 1 | 1 | 1 |

TABLE 2-continued

| INCI | Comp. 7 | Comp. 8 | Comp. 9 | Comp. C | Comp. D | Comp. E | Comp. F | Comp. G |
|---|---|---|---|---|---|---|---|---|
| Ethanol | 30 | 30 | 30 | 30 | 30 | 30 | 30 | 30 |
| Diisopropyl Adipate | 3 | 3 | 4 | 3 | 4 | 3 | 2 | |
| Ethyl Methicone | 37 | 34.5 | 32 | 33 | 31 | 32 | 33 | 35 |
| Dimethicone (20 cst) | | 2.5 | 4 | 4 | 5 | 5 | 5 | 5 |

The compositions were prepared as follows.

Main Phase: Added Ethanol, Octisalate, Homosalate, and Octocrylene into the main vessel and begin mixing at 300 rpm. While mixing, added Acrylates/Octylacrylamide Copolymer and Avobenzone and mixed until uniform. Once uniform added Dimethicone; Acrylates/Dimethicone Copolymer, Dimethicone (and) Trisiloxane or Ethyl Methicone (where appropriate), Diisopropyl Adipate, and Tocopheryl Acetate (where appropriate) and continued to mix. Once clear, added Dimethicone (20 cst) with continuous mixing. The compositions were tested for transparency. Transparency was determined using a 20 mL glass scintillation vial by visual observation. Compositions according to the invention were free of undissolved particles and clear. The comparative compositions were hazy and unstable.

The results are shown in Table 3.

TABLE 3

| | Solvent (weight percent) | | Dimethicone | |
|---|---|---|---|---|
| Composition | Dimethicone (and) Trisiloxane | Ethyl Methicone | (20 cst) (weight percent) | Transparency Test Result |
| 1 | 31.8 | | 5 | Clear |
| 2 | 34.3 | | 2.5 | Clear |
| 3 | 29.3 | | 7.5 | Clear |
| 4 | 26.8 | | 10 | Clear |
| 5 | 24.3 | | 12.5 | Clear |
| 6 | 23.3 | | 13.5 | Clear |
| A | 22.8 | | 14 | Hazy |
| B | 21.8 | | 15 | Hazy |
| 7 | | 37 | | Clear |
| 8 | | 34.5 | 2.5 | Clear |
| 9 | | 32 | 4 | Clear |
| C | | 33 | 4 | Hazy |
| D | | 31 | 5 | Hazy |
| E | | 32 | 5 | Hazy |
| F | | 33 | 5 | Hazy |
| G | | 35 | 5 | Hazy |

Compositions 1-6 according to the invention, containing a combination of up to 13.5 wt % of Dimethicone (20 cst) and at least 23.3 wt % Dimethicone (and) Trisiloxane according to the invention were clear. However, comparative Compositions A and B containing above 13.5 wt % Dimethicone (20 cst) were unstable and hazy.

Similarly, compositions 7-9 according to the invention, containing a combination of up to 4 wt % of Dimethicone (20 cst) and at least 32 wt % Ethyl Methicone were also clear. However, when the concentration of Dimethicone (20 cst) exceeded 4%, the compositions turned hazy, as shown by comparative Compositions C-G.

EXAMPLE 2

A series of compositions were made using 30 wt % Ethanol, Dimethicone (50 cst), either Dimethicone (and) Trisiloxane or Ethyl Methicone, and the other ingredients shown in Table 4. Compositions 10-14 were according to the invention and Compositions H-J were comparative.

TABLE 4

| INCI | Comp. 10 | Comp. 11 | Comp. 12 | Comp. 13 | Comp. 14 | Comp. H | Comp. HH | Comp. I | Comp. J |
|---|---|---|---|---|---|---|---|---|---|
| Avobenzone | 3 | 3 | 3 | 3 | 3 | 3 | 3 | 3 | 3 |
| Octisalate | 5 | 5 | 5 | 5 | 5 | 5 | 5 | 5 | 5 |
| Homosalate | 10 | 10 | 10 | 10 | 10 | 10 | 10 | 10 | 10 |
| Octocrylene | 10 | 10 | 10 | 10 | 10 | 10 | 10 | 10 | 10 |
| Acrylates/ Octylacrylamide Copolymer | 1 | 1 | 1 | 1 | 1 | 1 | 1 | 1 | 1 |
| Dimethicone; Acrylates/ Dimethicone Copolymer | 1 | 1 | 1 | 1 | 1 | 1 | 1 | 1 | 1 |
| Ethanol | 30 | 30 | 30 | 30 | 30 | 30 | 30 | 30 | 30 |
| Dimethicone (and) Trisiloxane | 31 | 31 | 31 | 31 | | 30 | | | |
| Diisopropyl Adipate | 6 | 4 | 1.5 | 6.5 | | 6 | | 5 | 4 |

TABLE 4-continued

| | Weight (%) | | | | | | | | |
|---|---|---|---|---|---|---|---|---|---|
| INCI | Comp. 10 | Comp. 11 | Comp. 12 | Comp. 13 | Comp. 14 | Comp. H | Comp. HH | Comp. I | Comp. J |
| Ethyl Methicone | | | | | 31 | | 31 | 31 | 31 |
| Dimethicone (50 cst) | 3 | 5 | 7.5 | 9 | 2.5 | 10 | 3 | 4 | 5 |

The compositions were prepared as follows.

Main Phase: Added Ethanol, Octisalate, Homosalate, and Octocrylene into the main vessel and began mixing at 300 rpm. While mixing, added Acrylates/Octylacrylamide Copolymer and Avobenzone and mixed until uniform. Once uniform added Dimethicone; Acrylates/Dimethicone Copolymer, Dimethicone (and) Trisiloxane or Ethyl Methicone (where appropriate), Diisopropyl Adipate, and continued to mix. Once clear, added Dimethicone (50 cst) with continuous mixing.

The compositions were tested for transparency as described in Example 1.

The results are shown in Table 5.

TABLE 5

| | Solvent (weight percent) | | Dimethicone | |
|---|---|---|---|---|
| Composition | Dimethicone (and) Trisiloxane | Ethyl Methicone | (50 cst) (weight percent) | Transparency Test Result |
| 10 | 31 | | 3 | Clear |
| 11 | 31 | | 5 | Clear |
| 12 | 31 | | 7.5 | Clear |
| 13 | 31 | | 9 | Clear |
| 14 | | 31 | 2.5 | Clear |
| H | 31 | | 10 | Hazy |
| HH | | 31 | 3 | Hazy |
| I | | 31 | 4 | Hazy |
| J | | 31 | 5 | Hazy |

Compositions 10-13 according to the invention, containing a combination of up to 9 wt % of Dimethicone (50 cst) and 31 wt % Dimethicone (and) Trisiloxane according to the invention were clear.

Similarly, Composition 14 according to the invention containing a combination of 2.5 wt % Dimethicone (50 cst) and 31 wt % of Ethyl Methicone was also clear.

However, comparative Composition H containing 10 wt % of Dimethicone (50 cst) 31 wt % Dimethicone (and) Trisiloxane was hazy. Comparative Compositions HH-J containing 31 wt % of Ethyl Methicone with 3, 4, and 5 wt % of Dimethicone (50 cst), respectively, were also hazy.

EXAMPLE 3

A series of compositions were made using 30 wt % Ethanol, Dimethicone (100 cst), either Dimethicone (and) Trisiloxane or Ethyl Methicone, and the other ingredients shown in Table 6. Composition 15 was according to the invention and Compositions K-S were comparative.

TABLE 6

| | Weight (%) | | | | | | | | |
|---|---|---|---|---|---|---|---|---|---|
| INCI | Comp. 15 | Comp. K | Comp. L | Comp. M | Comp. N | Comp. O | Comp. P | Comp. Q | Comp. S |
| Avobenzone | 3 | 3 | 3 | 3 | 3 | 3 | 3 | 3 | 3 |
| Octisalate | 5 | 5 | 5 | 5 | 5 | 5 | 5 | 5 | 5 |
| Homosalate | 10 | 10 | 10 | 10 | 10 | 10 | 10 | 10 | 10 |
| Octocrylene | 10 | 10 | 10 | 10 | 10 | 10 | 10 | 10 | 10 |
| Acrylates/Octylacrylamide Copolymer | 1 | 1 | 1 | 1 | 1 | 1 | 1 | 1 | 1 |
| Dimethicone; Acrylates/Dimethicone Copolymer | 1 | 1 | 1 | 1 | 1 | 1 | 1 | 1 | 1 |
| Ethanol | 30 | 30 | 30 | 30 | 30 | 30 | 30 | 30 | 30 |
| Dimethicone (and) Trisiloxane | 31 | 31 | 31 | 31 | 30.3 | 29.3 | 26.8 | | |
| Diisopropyl Adipate | 7 | 6 | 5 | 4 | 3 | 3 | 3 | 7 | 4 |
| Ethyl Methicone | | | | | | | | 31 | 31 |
| Tocopheryl Acetate | | | | | 0.2 | 0.2 | 0.2 | | |
| Dimethicone (100 cst) | 2 | 3 | 4 | 5 | 6.5 | 7.5 | 10 | 2 | 5 |

The compositions were prepared as follows.

Main Phase: Added Ethanol, Octisalate, Homosalate, and Octocrylene into the main vessel and began mixing at 300 rpm. While mixing, added Acrylates/Octylacrylamide Copolymer and Avobenzone and mixed until uniform. Once uniform added Dimethicone; Acrylates/Dimethicone Copolymer, Dimethicone (and) Trisiloxane or Ethyl Methicone (where appropriate), Diisopropyl Adipate, and Tocopheryl Acetate (where appropriate) and continued to mix. Once clear, added Dimethicone (100 cst) with continuous mixing.

The compositions were tested for transparency as described in Example 1.

The results are shown in Table 7.

TABLE 7

| | Solvent (weight percent) | | Dimethicone | |
| --- | --- | --- | --- | --- |
| Composition | Dimethicone (and) Trisiloxane | Ethyl Methicone | (100 cst) (weight percent) | Transparency Test Result |
| 15 | 31 | | 2 | Clear |
| K | 31 | | 3 | Hazy |
| L | 31 | | 4 | Hazy |
| M | 31 | | 5 | Hazy |
| N | 30.3 | | 6.5 | Hazy |
| O | 29.3 | | 7.5 | Hazy |
| P | 26.8 | | 10 | Hazy |
| Q | | 31 | 2 | Hazy |
| S | | 31 | 5 | Hazy |

Only Composition 15 according to the invention containing 31 wt % Dimethicone (and) Trisiloxane and Dimethicone (100 cst) was clear.

EXAMPLE 4

A series of compositions were made using 25 wt % Ethanol, Dimethicone (20 cst), either Dimethicone (and) Trisiloxane or Ethyl Methicone, and the other ingredients shown in Table 8. Compositions 16-18 were according to the invention and Compositions T-W were comparative.

The compositions were prepared as follows.

Main Phase: Added Ethanol, Octisalate, Homosalate, and Octocrylene into the main vessel and began mixing at 300 rpm. While mixing, added Acrylates/Octylacrylamide Copolymer and Avobenzone and mixed until uniform. Once uniform added Dimethicone; Acrylates/Dimethicone Copolymer, Dimethicone (and) Trisiloxane or Ethyl Methicone (where appropriate), Diisopropyl Adipate, and Tocopheryl Acetate (where appropriate) and continued to mix. Once clear, added Dimethicone (20 cst) with continuous mixing.

The compositions were tested for transparency as described in Example 1.

The results are shown in Table 9.

TABLE 9

| | Solvent (weight percent) | | Dimethicone | |
| --- | --- | --- | --- | --- |
| Composition | Dimethicone (and) Trisiloxane | Ethyl Methicone | (20 cst) (weight percent) | Transparency Test Result |
| 16 | 36.8 | | 5 | Clear |
| 17 | 35.8 | | 6 | Clear |
| 18 | 34.8 | | 7 | Clear |
| T | 34.3 | | 7.5 | Hazy |
| U | 33.8 | | 8 | Hazy |
| V | 31.8 | | 10 | Hazy |
| W | | 31 | 5 | Hazy |

As shown in Table 9, combination of 25% Ethanol and Dimethicone (and) Trisiloxane can solubilize up to 7 wt % of Dimethicone (20 cst), so the sunscreen composition remained clear and exhibiting a good aesthetic feel, as shown by Compositions 16-18. When the concentration of Dimethicone (20 cst) exceeded 7%, the sunscreen formulation was unstable and turned hazy as shown by Compositions T-V. The combination of 25% Ethanol and Ethyl Methicone failed to solubilize 5 wt % of Dimethicone (20 cst), as shown in composition W.

TABLE 8

| | Weight (%) | | | | | | |
| --- | --- | --- | --- | --- | --- | --- | --- |
| INCI | Comp. 16 | Comp. 17 | Comp. 18 | Comp. T | Comp. U | Comp. V | Comp. W |
| Avobenzone | 3 | 3 | 3 | 3 | 3 | 3 | 3 |
| Octisalate | 5 | 5 | 5 | 5 | 5 | 5 | 5 |
| Homosalate | 10 | 10 | 10 | 10 | 10 | 10 | 10 |
| Octocrylene | 10 | 10 | 10 | 10 | 10 | 10 | 10 |
| Acrylates/ Octylacrylamide Copolymer | 1 | 1 | 1 | 1 | 1 | 1 | 1 |
| Dimethicone; Acrylates/ Dimethicone Copolymer | 1 | 1 | 1 | 1 | 1 | 1 | 1 |
| Ethanol | 25 | 25 | 25 | 25 | 25 | 25 | 25 |
| Dimethicone (and) Trisiloxane | 36.8 | 35.8 | 34.8 | 34.3 | 33.8 | 31.8 | |
| Diisopropyl Adipate | 3 | 3 | 3 | 3 | 3 | 3 | 9 |
| Ethyl Methicone | | | | | | | 31 |
| Tocopheryl Acetate | 0.2 | 0.2 | 0.2 | 0.2 | 0.2 | 0.2 | |
| Dimethicone (20 cst) | 5 | 6 | 7 | 7.5 | 8 | 10 | 5 |

EXAMPLE 5

A series of compositions were made using 20 or 25 wt % Ethanol, Dimethicone (20 or 50 or 100 cst), Dimethicone (and) Trisiloxane, and the other ingredients shown in Table 10. Compositions 19-21 were according to the invention and Compositions X-ZZ were comparative.

TABLE 10

| INCI | Weight (%) | | | | | | |
|---|---|---|---|---|---|---|---|
| | Comp. 19 | Comp. X | Comp. 20 | Comp. 21 | Comp. Y | Comp. Z | Comp. ZZ |
| Avobenzone | 3 | 3 | 3 | 3 | 3 | 3 | 3 |
| Octisalate | 5 | 5 | 5 | 5 | 5 | 5 | 5 |
| Homosalate | 10 | 10 | 10 | 10 | 10 | 10 | 10 |
| Octocrylene | 10 | 10 | 10 | 10 | 10 | 10 | 10 |
| Acrylates/ Octylacrylamide Copolymer | 1 | 1 | 1 | 1 | 1 | 1 | 1 |
| Dimethicone; Acrylates/ Dimethicone Copolymer | 1 | 1 | 1 | 1 | 1 | 1 | 1 |
| Ethanol | 25 | 25 | 25 | 25 | 25 | 20 | 20 |
| Dimethicone (and) Trisiloxane | 37 | 36 | 39.3 | 37.8 | 36.8 | 45.8 | 41.8 |
| Diisopropyl Adipate | 3 | 3 | 3 | 3 | 3 | 3 | 3 |
| Tocopheryl Acetate | | 0.2 | 0.2 | 0.2 | 0.2 | 0.2 | 0.2 |
| Dimethicone (20 cst) | | | | | | 1 | 5 |
| Dimethicone (50 cst) | 5 | 6 | | | | | |
| Dimethicone (100 cst) | | | 2.5 | 4 | 5 | | |

The compositions were prepared as follows.

Main Phase: Added Ethanol, Octisalate, Homosalate, and Octocrylene into the main vessel and began mixing at 300 rpm. While mixing, added Acrylates/Octylacrylamide Copolymer and Avobenzone and mixed until uniform. Once uniform added Dimethicone; Acrylates/Dimethicone Copolymer, Dimethicone (and) Trisiloxane, Diisopropyl Adipate, and Tocopheryl Acetate (where appropriate) and continued to mix. Once clear, added the appropriate Dimethicone (20 cst, 50 cst, or 100 cst), with continuous mixing.

The compositions were tested for transparency as described in Example 1.

The results are shown in Table 11.

As shown in Table 11, combination of 25% ethanol and Dimethicone (and) Trisiloxane can solubilize up to 5 wt % of Dimethicone (50 cst) and up to 4 wt % of Dimethicone (100 cst), such that the sunscreen composition remained clear and exhibiting a good aesthetic feel, as shown in compositions 19-21. When the concentration of Dimethicone (50 cst) exceeded 6% or Dimethicone (100 cst) exceeded 5%, the sunscreen formulation was unstable and turned hazy as shown in compositions X and Y. Further, combination of 20% ethanol and Dimethicone (and) Trisiloxane failed to solubilize 1 wt % of Dimethicone (20 cst), as shown in compositions Z-ZZ.

The invention claimed is:

1. A sunscreen composition comprising homosalate, octisalate, avobenzone, octocrylene, about 30 weight percent ethanol, about 5 weight percent of dimethicone having a viscosity of 20 centistokes as measured by ASTM Designation: D4283-98—Standard Test Method for Viscosity of Silicone Fluids, and about 31.8 weight percent of dimethicone (and) trisiloxane having a viscosity of 2 centistokes as

TABLE 11

| Composition | Weight percent | | | | Transparency Test Result |
|---|---|---|---|---|---|
| | Dimethicone (and) Trisiloxane | Dimethicone (20 cst) | Dimethicone (50 cst) | Dimethicone (100 cst) | |
| 19 | 37 | | 5 | | Clear |
| 20 | 39.3 | | | 2.5 | Clear |
| 21 | 37.8 | | | 4 | Clear |
| X | 36 | | 6 | | Hazy |
| Y | 36.8 | | | 5 | Hazy |
| Z | 45.8 | 1 | | | Hazy |
| ZZ | 41.8 | 5 | | | Hazy | measured by ASTM Designation: D4283-98—Standard Test Method for Viscosity of Silicone Fluids, wherein the composition is anhydrous and transparent.

2. The composition of claim 1 substantially free of oxybenzone.

* * * * *